United States Patent
Van Valey

(10) Patent No.: US 7,597,555 B2
(45) Date of Patent: Oct. 6, 2009

(54) DENTAL ARTICULATOR EXTENDER

(76) Inventor: Edwin T. Van Valey, 95 Concord Rd., Sudbury, MA (US) 01776

( * ) Notice: Subject to any disclaimer, the term of this patent is extended or adjusted under 35 U.S.C. 154(b) by 277 days.

(21) Appl. No.: 11/278,614

(22) Filed: Apr. 4, 2006

(65) Prior Publication Data

US 2006/0234181 A1    Oct. 19, 2006

Related U.S. Application Data

(60) Provisional application No. 60/669,728, filed on Apr. 8, 2005.

(51) Int. Cl.
*A61C 11/00* (2006.01)

(52) U.S. Cl. .......................... 433/54; 433/54
(58) Field of Classification Search .............. 433/54–67, 433/215, 229
See application file for complete search history.

(56) References Cited

U.S. PATENT DOCUMENTS

| 5,622,497 A | * | 4/1997 | Cho ..................... 433/60 |
| 5,957,688 A | | 9/1999 | Van Valey |
| 6,402,512 B1 | | 6/2002 | Van Valey |
| 6,499,999 B1 | | 12/2002 | Van Valey |
| 6,705,864 B2 | | 3/2004 | Van Valey |

* cited by examiner

*Primary Examiner*—Cris L Rodriguez
*Assistant Examiner*—Hao D Mai
(74) *Attorney, Agent, or Firm*—Hamilton, Brook, Smith & Reynolds, P.C.

(57) ABSTRACT

An extender device connects between the halves of an articulator thereby increasing the width of the articulator while still allowing the articulator to be handled as one piece during its application to the models. In an embodiment, the extender device is of a snap-fit design.

4 Claims, 10 Drawing Sheets

DENTAL ARTICULATOR EXTENDER

RELATED APPLICATION

This application claims the benefit of U.S. Provisional Application No. 60/669,728, filed Apr. 8, 2005. The entire teachings of the above application are incorporated herein by reference.

BACKGROUND

In the fabrication of dental prosthetics, such as false teeth or caps, a negative impression is made of the teeth of a dental patient using a thermoplastic material. The negative impression is then filled with a hardenable material to form a die. The die is affixed to a base formed of similar hardenable material to form a dental model. A dental model articulator is used to correlate upper and lower dental models in the forming and adjustment of the dental prosthesis.

The appeal of using a one-use or dispensable articulator is one primarily of time. A reusable articulator needs to be mounted to the models of the teeth with dental plaster, which requires considerable time in the processes of mixing, placing, curing, clean-up and then the subsequent removal of the hardened plaster from the models and articulator after completion of the prosthesis so as to allow re-use of the articulator. Dispensable articulators can save the time involved with these steps and have the added advantages of allowing the completed work to be returned to the dentist still articulated to allow verification of the mounting and to increase the presentation value of the case. Typically, a one-use articulator is secured to the dental models using an adhesive, thereby eliminating the use of plaster. To allow this, the articulator must provide a mechanism to adapt glueable members to angular differences of surfaces on the models. Such a mechanism is not needed as part of a reusable articulator because its members are allowed a large range of angular and positional differences within the masses of plaster that are used to affix the articulator to the models.

U.S. Pat. Nos. 5,957,688; 6,499,999 and 6,705,864 disclose a single-use dental articulator which employs a hinge joint that uses an integrated locking mechanism. This locking mechanism allows for the articulator to provide sliding-type translatory motions in the released mode as well as accurate centric-type positioning of the dental models when the locking mechanism is engaged.

SUMMARY

Articulators of the type disclosed in U.S. Pat. Nos. 5,957, 688; 6,499,999 and 6,705,864 are typically made of a plastic resin. For such devices there may exist a certain amount of "play" even in the locked mode due to the deflection of the "cymbal" elements of the hinge joint when a lateral motion is applied between the jaw segments of the dental models. This deflection allows a corresponding lateral motion within the hinge joint which is evidenced by motions out of the centric position between the two models. Although this is not typically a severe problem, there can be certain cases when more centric stability is desired.

When lateral force is applied between the opposing models, the motion appears as a rotation about an axis that is perpendicular to the occlusal plane and between the two hinge joints of the articulator. U.S. Pat. No. 6,402,512 describes a device which can be applied to the articulator hinge joint which physically constrains the non-axial motion in the joint to effect more stability. This requires separate devices be applied and removed from the articulator to lock and release the joints.

The present approach reduces this undesired motion by widening the distance between the two hinge joints thereby increasing the radius to the aforementioned perpendicular axis of effective rotation. Lengthening this radius then amplifies the required amount of motion between the halves of each hinge joint to allow a similar amount of lateral displacement of the models from the centric position.

In accordance with the present approach, an extender device connects between the halves of the articulator thereby increasing the width of the same articulator while still allowing the articulator to be handled as one piece during its application to the models. In an embodiment, the extender device is of a snap-fit design.

Accordingly, a dental model articulator comprises a pair of arms, each arm having a first arm segment and a second arm segment, the first arm segment terminating at its distal end in a first arm connection element that is pivotably engageable with one of first and second dental models and terminating at its proximal end in a node element, the second arm segment terminating at its distal end in a second arm connection element that is pivotably engageable with the other of the first and second dental models and terminating at its proximal end in a retaining element, the retaining element receiving the node element to define a hinge joint; the articulator further comprises a pair of extender elements, each extender element connecting a pair of arm connection elements.

The present approach provides a more elegant solution to increase the stability of the articulator on the particular cases that may require more accuracy. This widening approach affords the technician more stability of the case during its manufacture while not hindering the convenience of the operation of the articulator.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION

Figure 1:
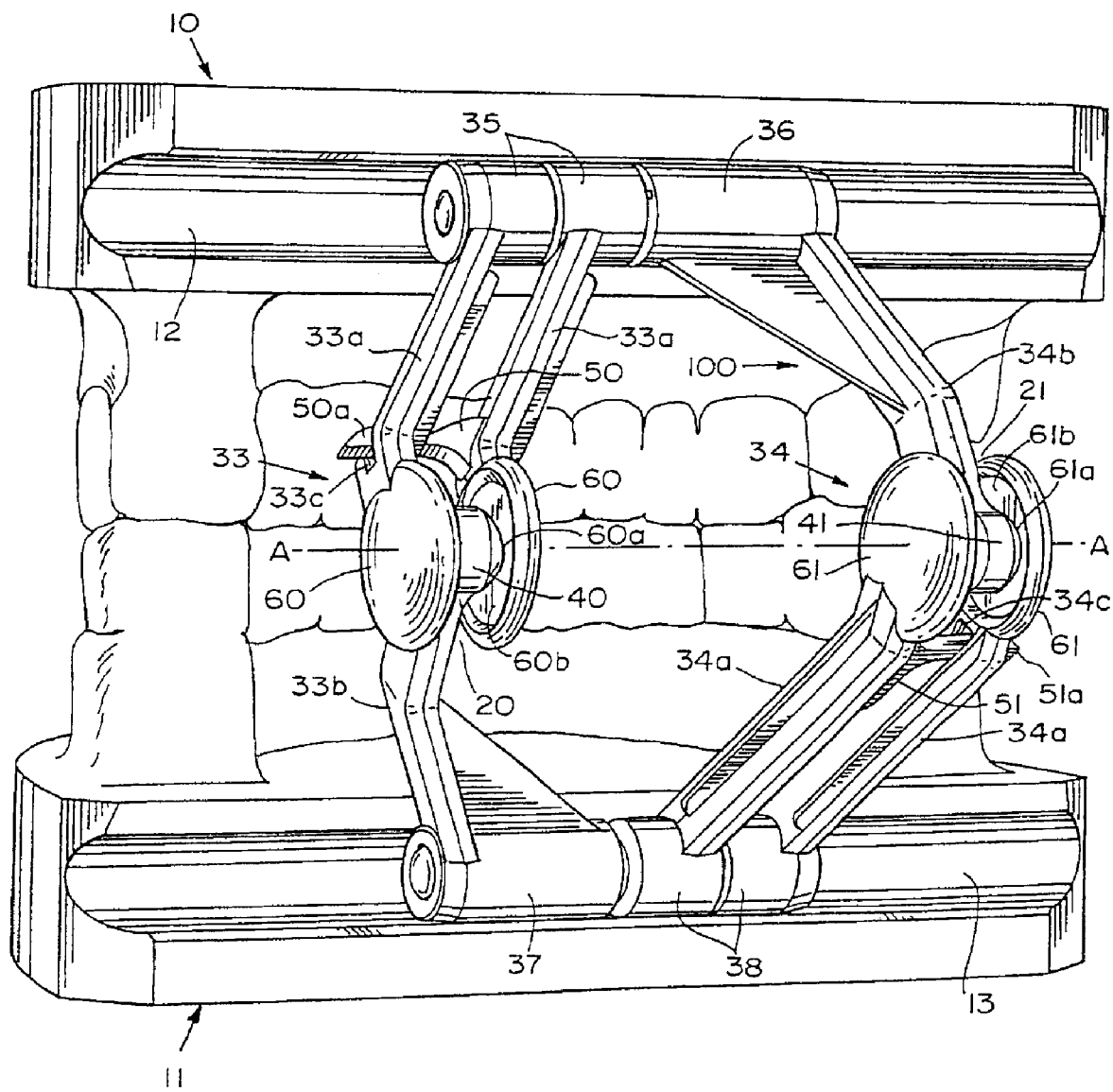
FIGS. 1 to 3 show perspective posterior, side and rear views, respectively, of a first embodiment of an articulator of the having two articulator arms mounted to full arch dental models.

Referring to FIGS. 1-4, an embodiment of an articulator 100 reintegrating a pair of full arch dental models 10 and 11 is there shown. The articulator 100 comprises a pair of arms 33, 34 that are identical in structure. It should be noted that the following description generally employs a pair of reference characters to refer to a particular element or feature of the respective arms. The arms 33, 34 each include an arm segment 33b, 34b and a pair of parallel, bifurcated arm segments 33a, 34a. The parallel arm segments 33a, 34a terminate at a distal end in cylindrical rod-like elements 35, 38 and at a proximal end in a pair of coaxial cymbals 60, 61. The arm segment 33b, 34b terminates at a distal end in cylindrical rod-like element 36, 37 and at a proximal end in node 40, 41. The node is retained between the pair of cymbals 60, 61 supported by the bifurcated arm segments 33a, 34a to form a hinge joint 20, 21.

Figure 3:
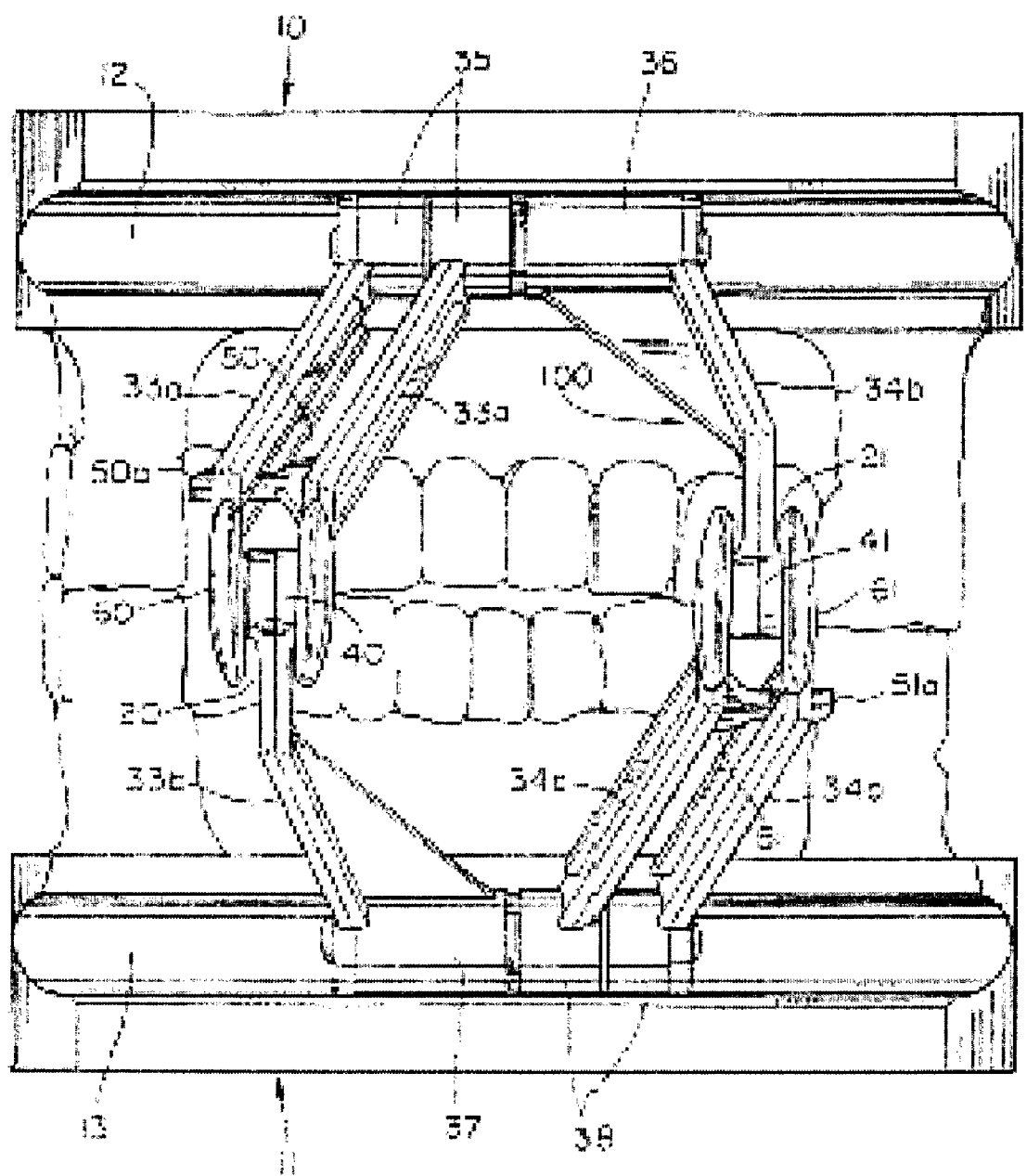
Figure 4:
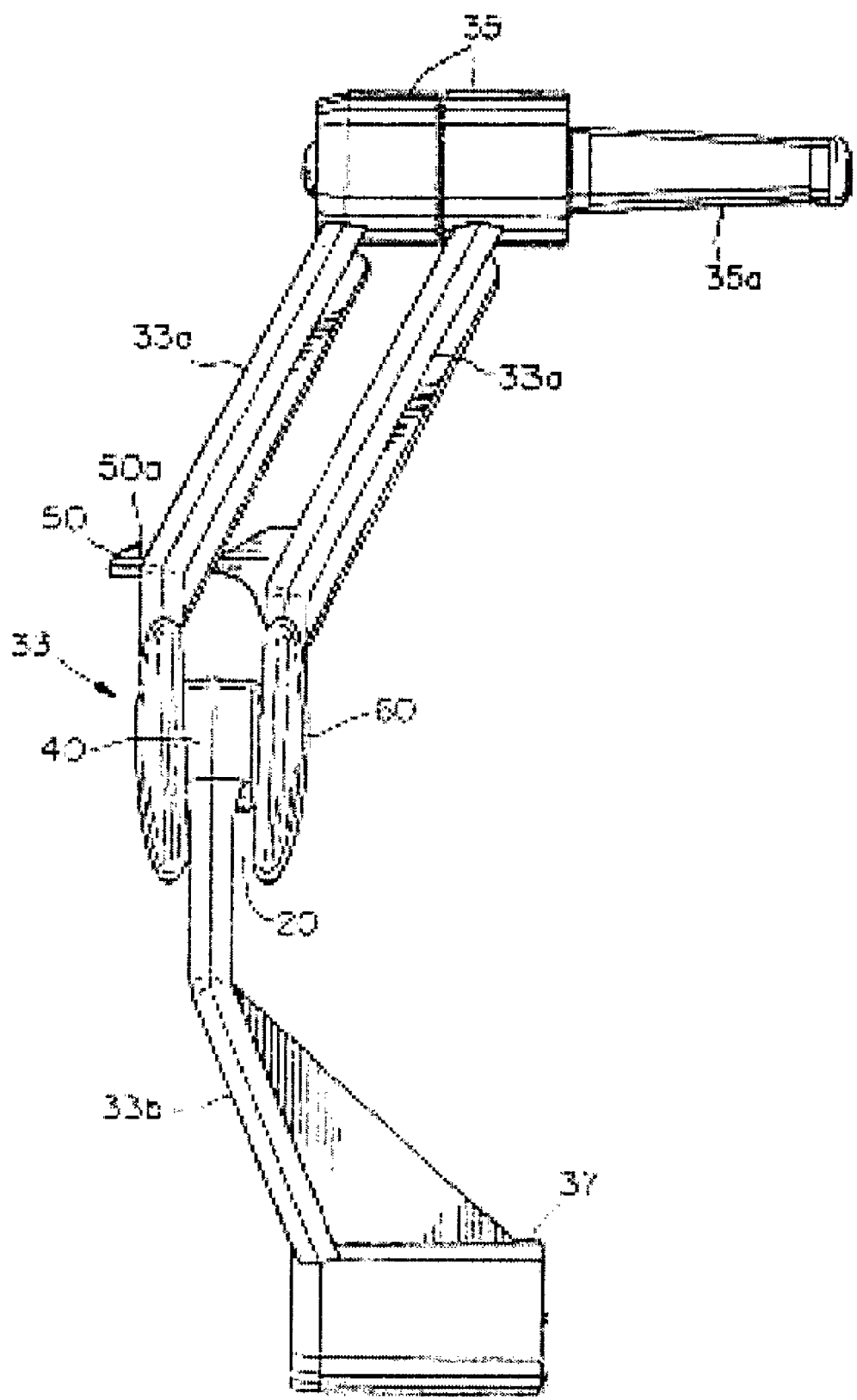
FIG. 4 is a rear view of one arm of the articulator of FIG. 1.
Figure 5:
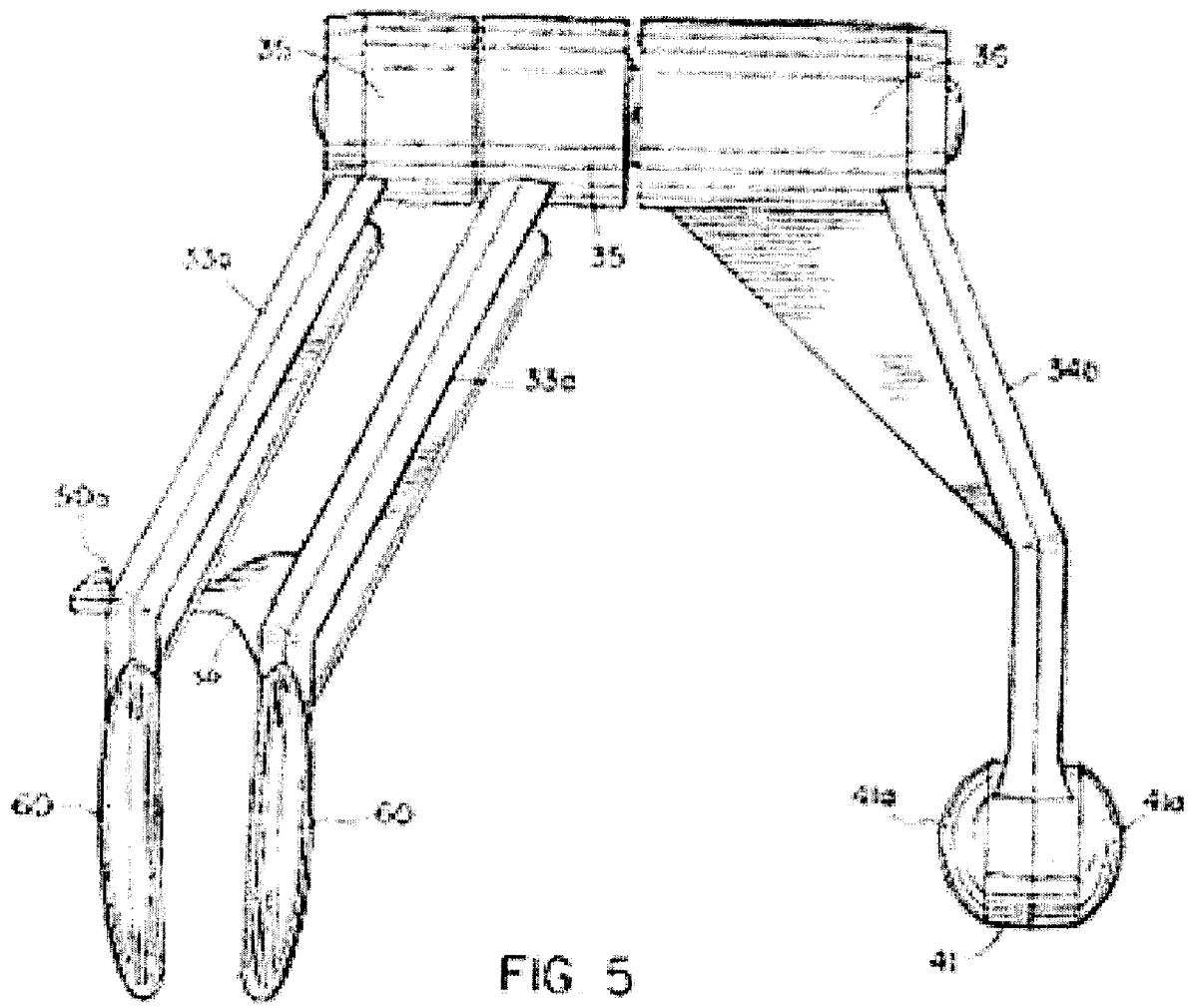
FIG. 5 is a rear view of either the upper or lower half of both arms of the articulator of FIG. 1 interconnected.

FIG. 4 illustrates arm 33 which is identical to arm 34. A preferred assembly of articulator 100 is formed by connecting the arms 33, 34 to each other in a complementary fashion to provide a single assembly for ease of handling. Specifically, the complementary connection is formed by snap-fitting cylindrical stem 35a into cylindrical rod-like element 36 and stem 38a into element 37 to form the articulator shown in FIGS. 1-3. Referring to FIG. 5, the portion of arm 33 that includes parallel arm segments 33a is shown connected to the portion of arm 34 that includes arm segment 34b.

A model connector defining a single axis pivot mechanism is incorporated into the base of each model 10, 11 in the form of transverse half-cylinders or channels 12 and 13 which traverse the posterior of the models (FIGS. 1 and 3). The channels can be either cut into the existing models or formed when the models are cast to provide connection at a range of angles about the radial axis of the transverse channels for mating the cylindrical rod-like elements 35, 36, 37, 38 which form the complement to these pivot mechanisms. While the channels 12, 13 are shown located on the posterior of the models, it is also possible to locate the channels at the top or bottom of the respective models. In alternate embodiments, the channels can instead be formed at the distal ends of the arm segments and the cylindrical elements can be incorporated in the models to provide the single axis connexus.

Figure 2:
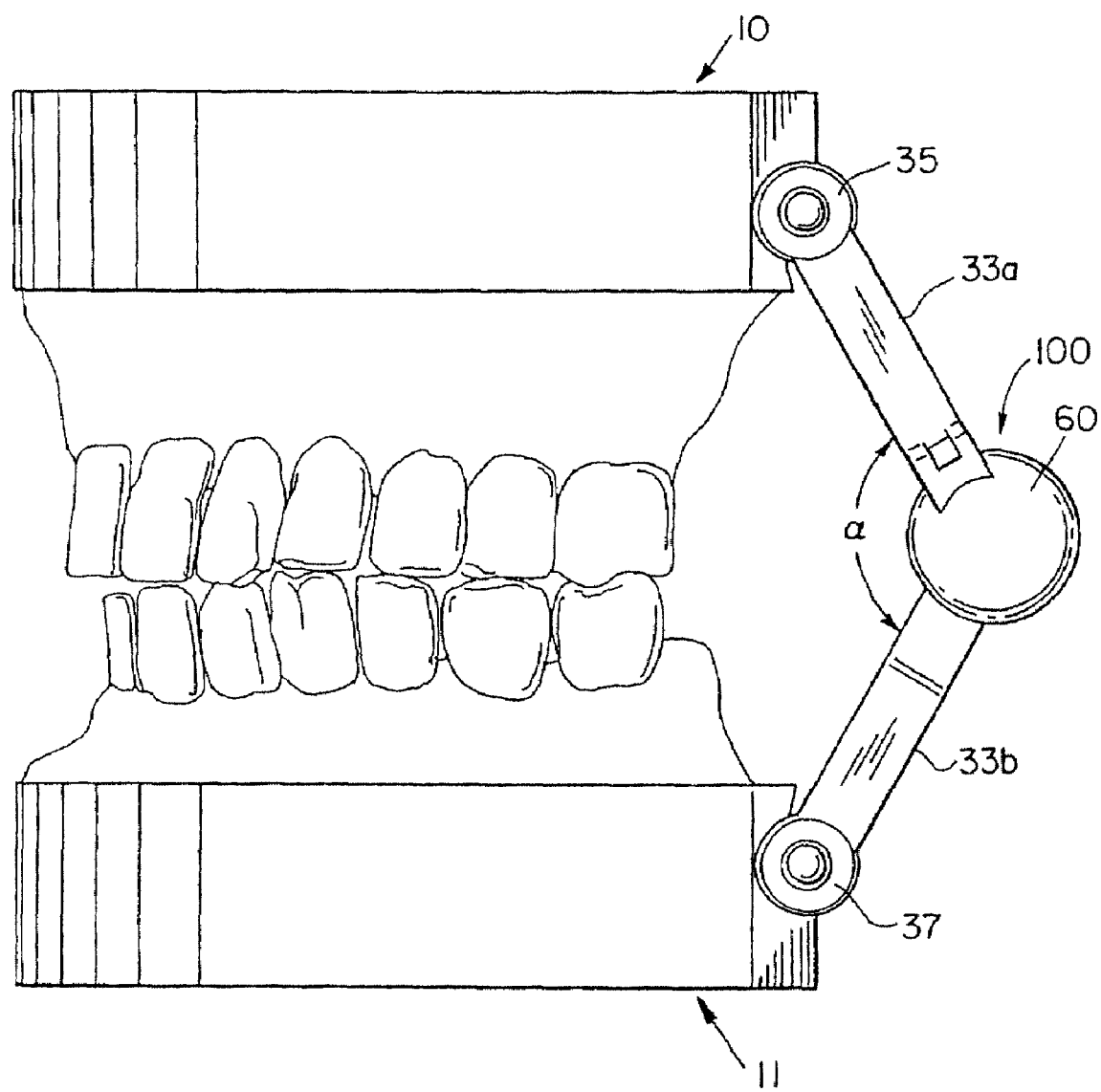

The cylindrical elements 35, 36, 37, 38 have sufficient transverse axial width such that any adjustment motion of the cylindrical elements within the channels is limited to radial motion about the channel axis and transverse motion along this axis. With the dental models placed at a closed and centric occlusal (i.e., closed bite) relationship as shown in FIG. 2, the arm segments of the respective arms intersect at an angle of between approximately 40 to 170 degrees, the angle being dependent upon the vertical distance between the models 10 and 11.

Figure 6:
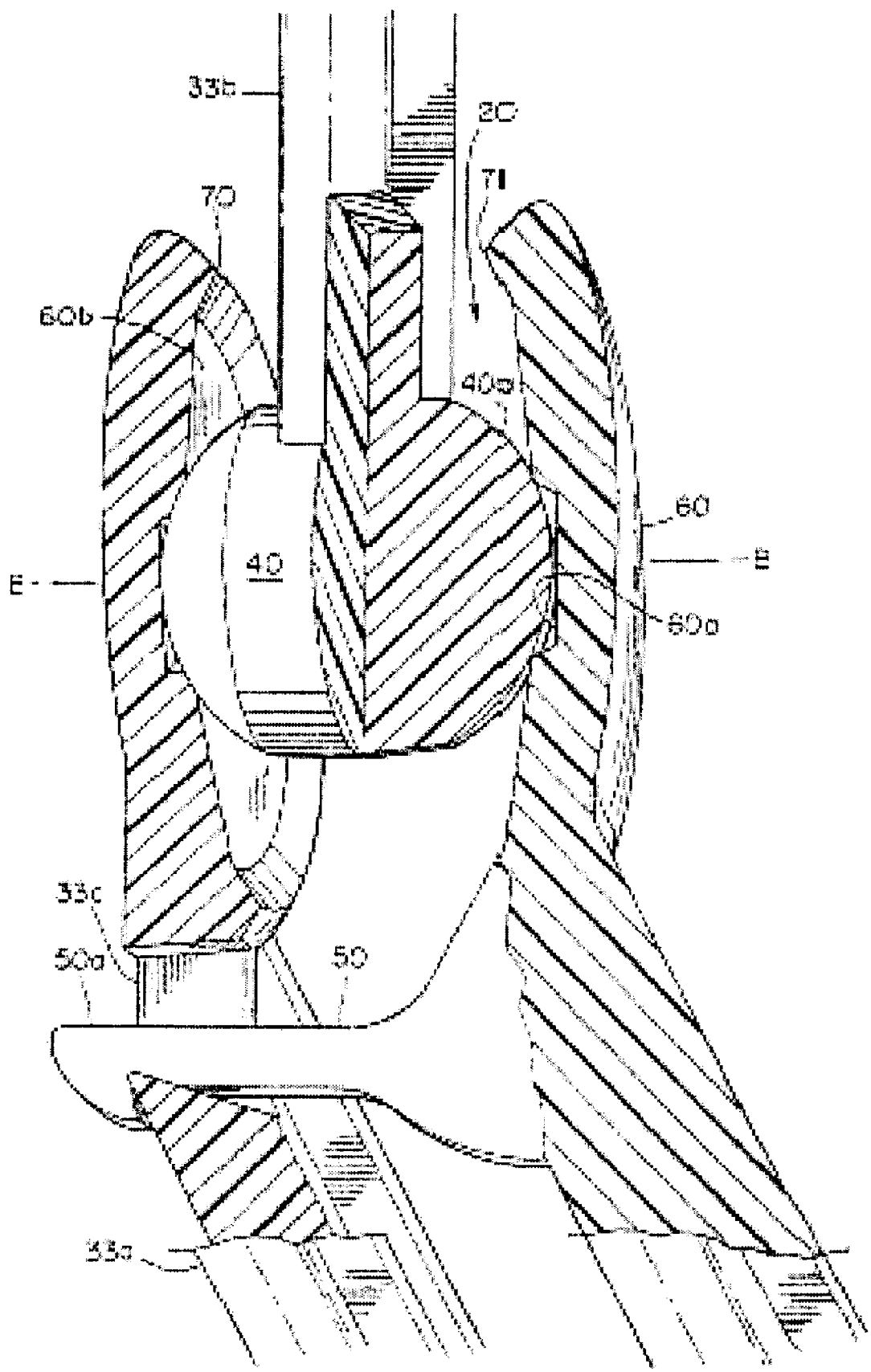
FIG. 6 is a partial cross-sectional view of one hinge joint of the articulator.

The multiaxial motion provided by the articulator will now be described. Referring again to FIG. 5, node 40, 41 includes two opposed outwardly facing convex portions 40a, 41a. Referring to FIG. 6, a partial cross-section of one joint 20 of the articulator is shown. The cymbals 60, 61 are concave and toroidal in shape. When the node 40, 41 is engaged with the cymbals 60, 61, the convex portions 40a, 41a of each node 40, 41 are held in depressions or detents 60a, 61a at the center of each cymbal by resilience of the material in the bifurcated arm segment 33a, 34a.

The primary rotational motion of the node between the parallel arm segments is radial to an axis B that is shared coaxially by the cymbals. Because node 40, 41 and its connected arm segment 33b, 34b has no fixed axis when captured between the cymbals 60, 61, hinging motion between the arm segment 33b, 34b and parallel arm segments 33a, 34a is allowed an amount of orthogonal deviation from the axis B, that is, motion is provided about a set of orthogonal axes. This multiaxial motion of the hinge joint 20, 21 allows the cylindrical connection elements 35, 36, 37, 38 at the extremities of the arms 33, 34 to align with the nonparallelism that is likely to exist between the channels 12, 13 of models 10, 11.

Multiaxial motion is only required and exhibited during alignment of the articulator 100 to the models. Once the two arms of the articulator 100 are affixed to the models, the only axial motion allowed by the articulator between the models is about a single axis A defined together by the two hinge joints 20, 21 (FIG. 1). This common transverse hinge axis A lies interjacent and posterior to the dental models 10, 11 and is approximately perpendicular to a sagittal plane of the models.

Each bifurcated arm segment 33a, 34a includes a resilient pawl or latch 50, 51 that is used to increase or decrease pressure (i.e., compression) on the node 40, 41 between the cymbals 60, 61. The pawl includes a hooked portion 50a, 51a for engagement through opening 33c, 34c in the bifurcated arm segment 33a, 34a. When the pawl is engaged, it increases the resilient pressure on the node between the cymbals to an amount that effectively limits or restrains any motion between the arm segments 33a, 33b and 34a, 34b to rotational motion about the common axis A. Releasing the pawl lessens the resilience to an amount such that protrusive and retrusive motions are permitted between the articulated models 10, 11 by allowing the cymbals to move apart, thereby permitting the convexities of the node to slide across the surfaces 60b, 61b of the cymbals. This free sliding motion is then limited in excursion by ridges 70, 71 at the periphery of the cymbals. Note that while the multiaxial motion about the hinge joints 20, 21 is used for alignment of the articulator, the free sliding motion is used for simulation of lateral and protrusive translatory motions once the articulator has been aligned and mounted to the models.

Figure 7A:
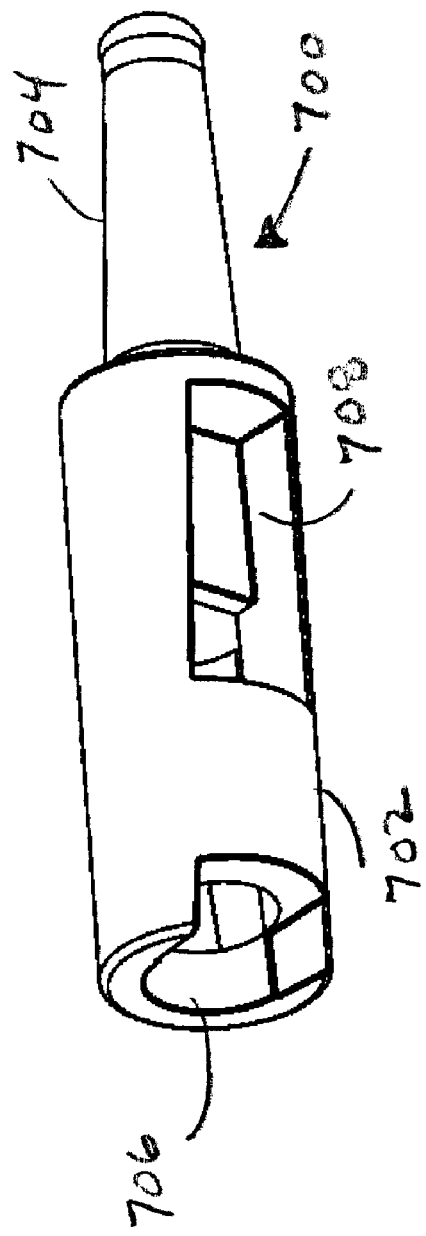
FIG. 7A is a front perspective view of an embodiment of an extender device.
Figure 7B:
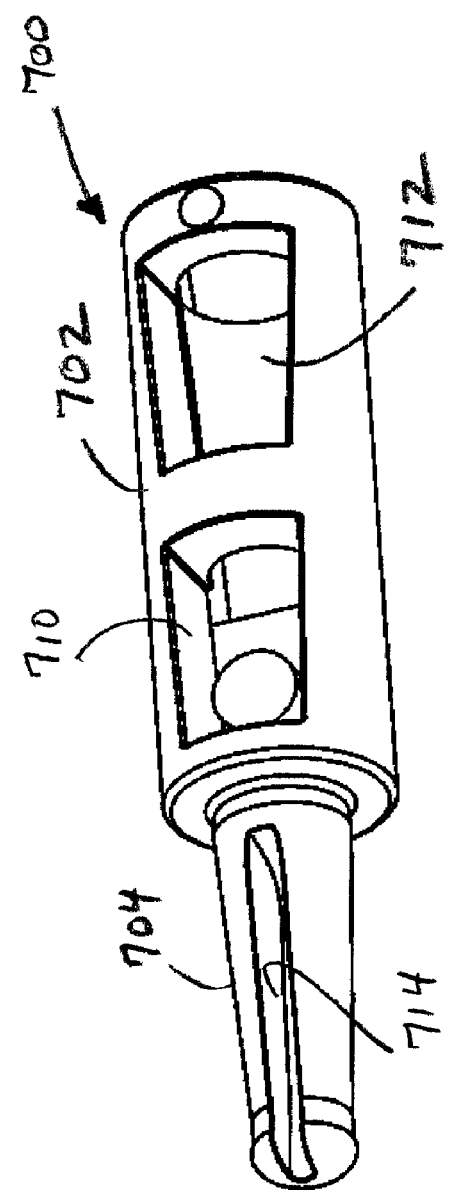
FIG. 7B is a rear perspective view of an embodiment of an extender device.
Figure 8:
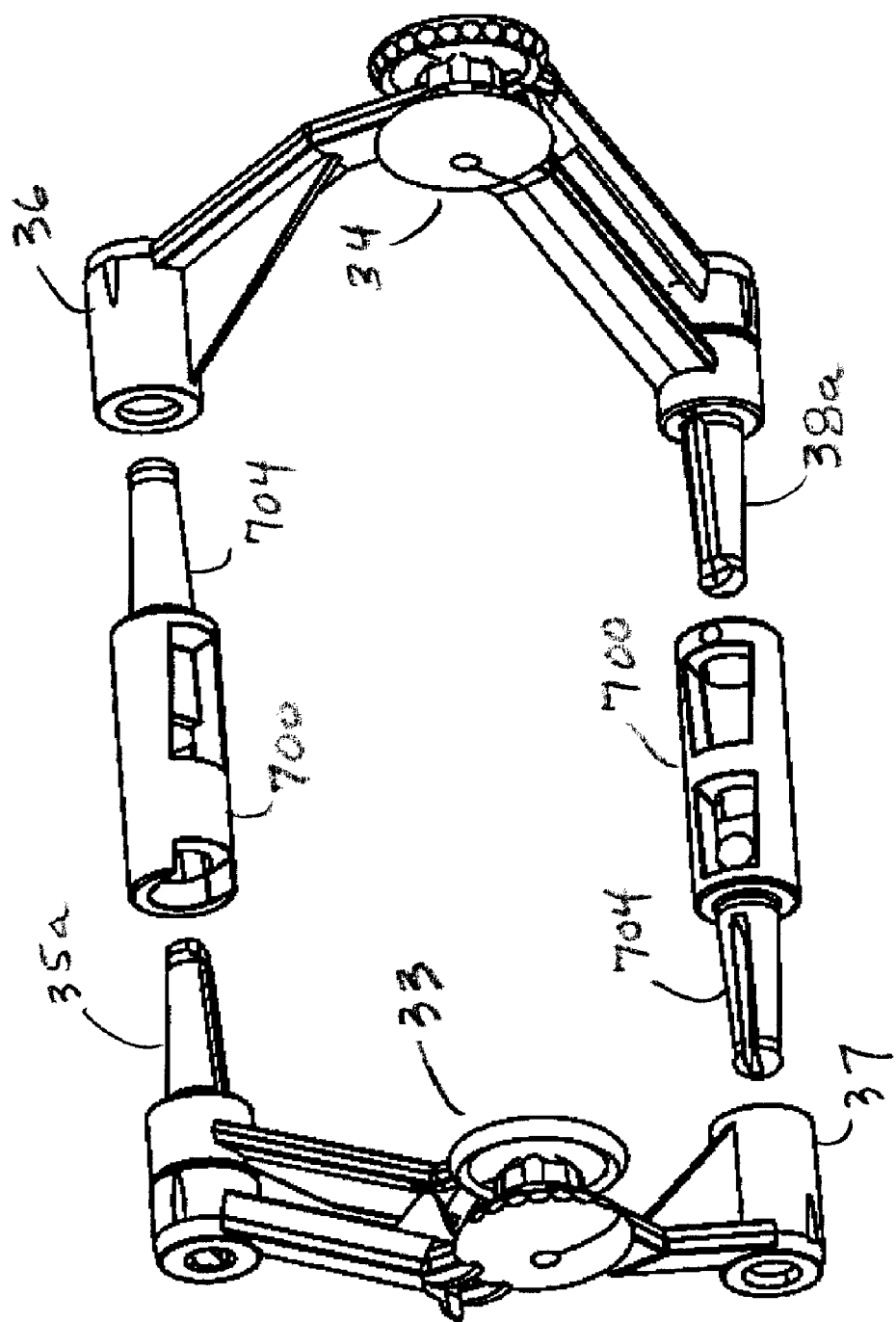
FIG. 8 is an exploded view of the extender device of FIGS. 7A and 7B in combination with a pair of articulator arms.
Figure 9:
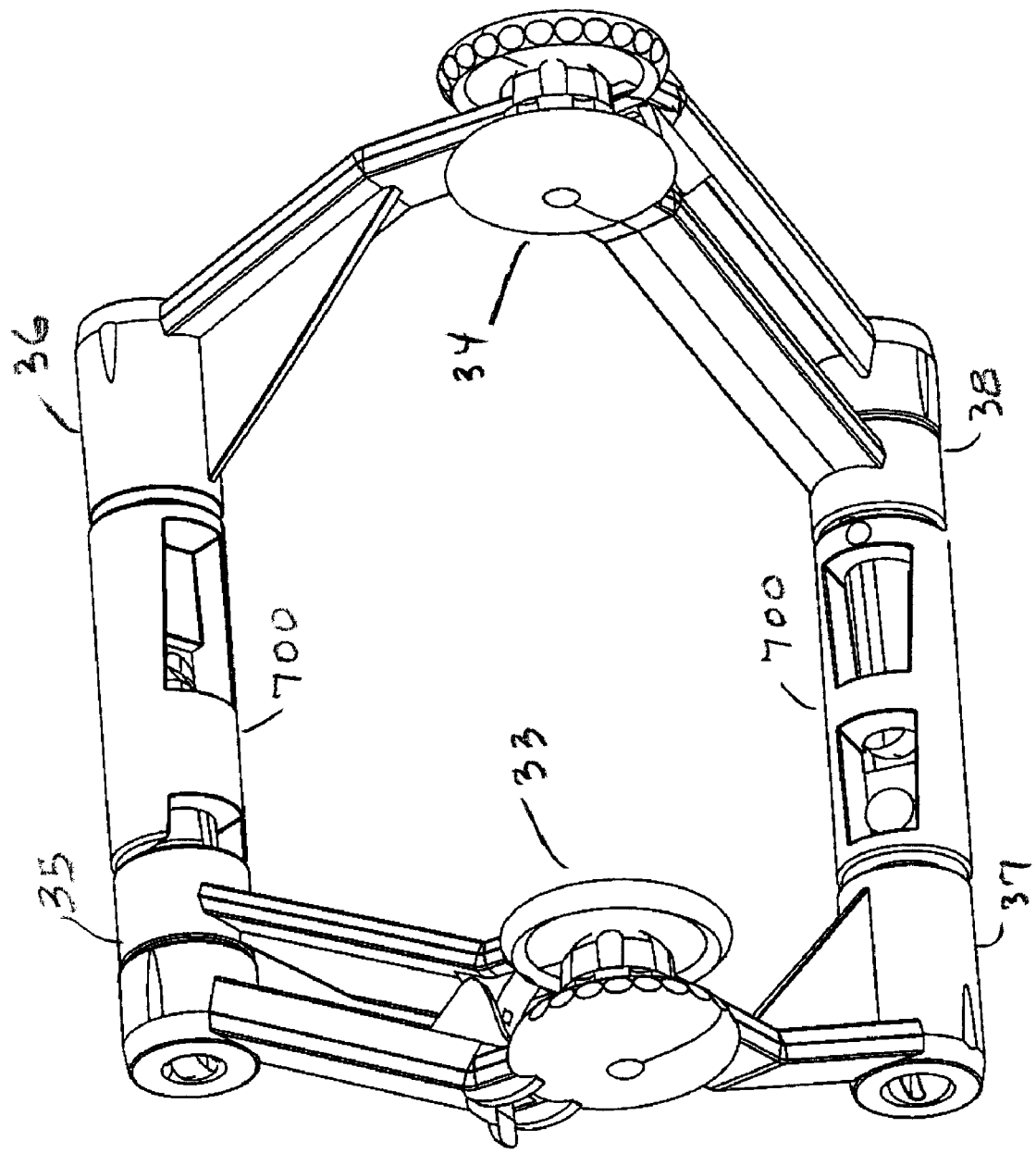
FIG. 9 is a perspective view of the assembled articulator of FIG. 8.

Reference is now made to FIGS. 7A and 7B, which show front and rear perspective views, respectively, of extender device 700. The extender device is a cylindrical rod-like element that includes cylindrical base 702 and snap-fitting cylindrical stem 704. The stem 704, having a slot 714 for resilience, snap-fits into cylindrical rod-like element 36 or 37 of respective arms 34, 33 (FIGS. 1-4). The base 702 has an opening 706 for receiving a snap-fitting cylindrical stem 35a or 38a of respective arms 33, 34 (FIGS. 1-4). As shown in the embodiment, the device also has optional mold insert openings 708, 710 and 712 for ease of manufacture. Exploded and assembled views are shown in FIGS. 8 and 9, respectively.

Figure 10:
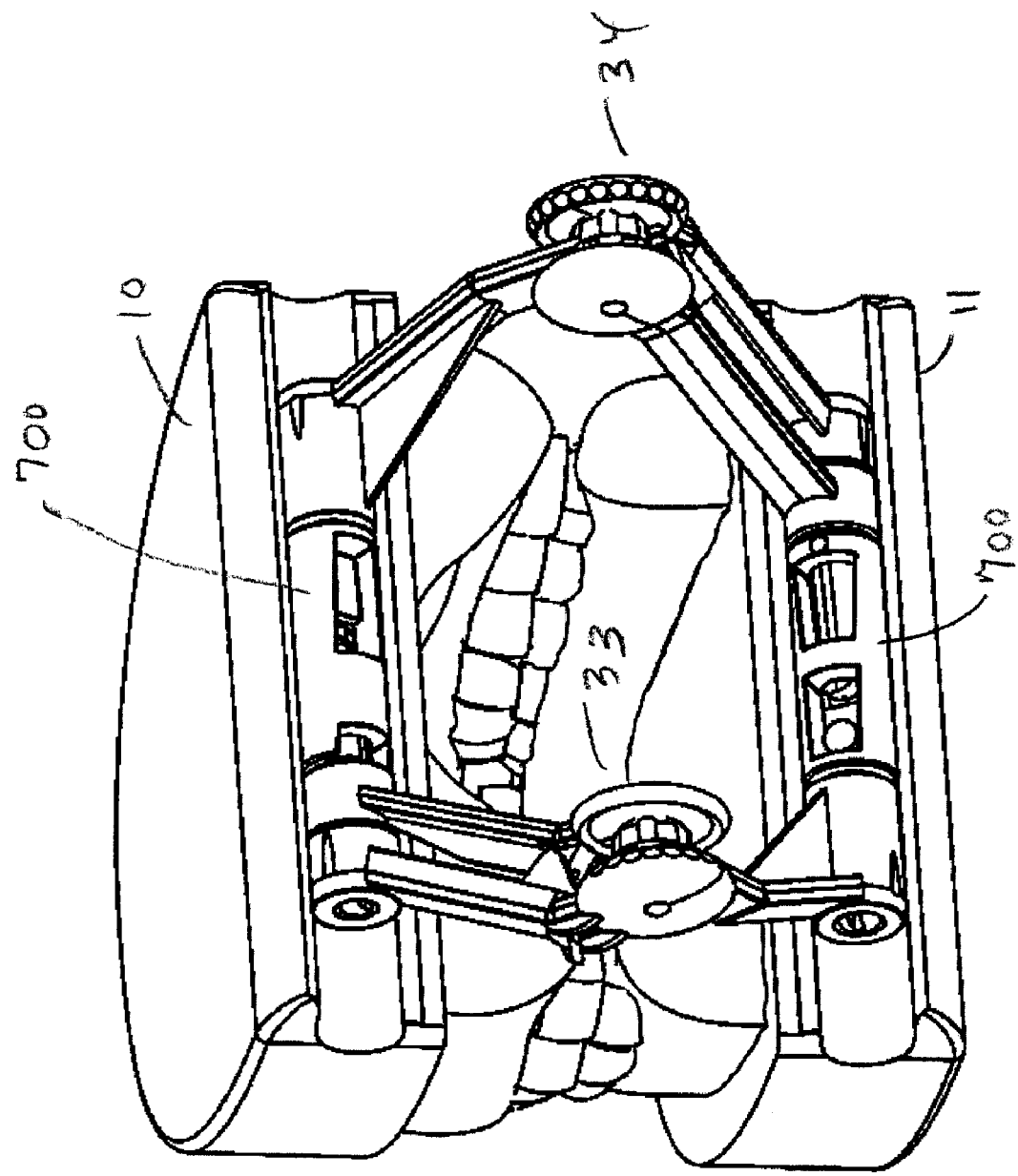
FIG. 10 is a perspective posterior view of the assembled articulator having two arms and respective extender devices mounted to full arch dental models.

FIG. 10 illustrates the assembled articulator with the extender devices 700 connecting the pair of arms 33, 34, with the assembly mounted to full arch dental models. With this arrangement, undesired motion is reduced by widening the distance between the hinge joint mechanism comprising the two hinge joints thereby increasing the radius to the perpendicular axis of effective rotation. Lengthening this radius then amplifies the required amount of motion between the halves of each hinge joint to allow a similar amount of lateral displacement of the models from the centric position.

It should be understood that in certain applications, the distance between the hinge joint mechanism may be further widened by connecting two or more extender devices together.

While this invention has been particularly shown and described with references to preferred embodiments thereof, it will be understood by those skilled in the art that various changes in form and details may be made therein without departing from the scope of the invention encompassed by the appended claims.

What is claimed is:

1. A dental model articulator comprising:
a first articulator half and a second articulator half, each articulator half having a first arm segment terminating at its distal end in a first arm connection element and terminating at its proximal end in a node element, and a second arm segment terminating at its distal end in a second arm connection element and terminating at its proximal end in a retaining element, the retaining element receiving the node element to define a hinge joint;
the first and second articulator halves connected solely by first and second extender elements at opposed ends of the extender elements, the first extender element connecting between the first arm connection element of the first articulator half and the second arm connection element of the second articulator half, and the second extender element connecting between the second arm connection element of the first articulator half and the first arm connection element of the second articulator half, the length of the first and second extender elements widening a distance between the first and second articulator halves.

2. The articulator of claim 1 wherein each extender element includes a base that connects to a stem of the corresponding first arm connection element and an extender stem that connects to a mating element of the corresponding second arm connection element.

3. The articulator of claim 2 wherein the connections between the extender elements and the arm connection elements are snap-fit connections.

4. The articulator of claim 1 wherein each extender element includes at least two connected extender devices.

* * * * *

UNITED STATES PATENT AND TRADEMARK OFFICE
CERTIFICATE OF CORRECTION

PATENT NO.       : 7,597,555 B2                                        Page 1 of 1
APPLICATION NO.  : 11/278614
DATED            : October 6, 2009
INVENTOR(S)      : Edwin T. Van Valey It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 278 days.

Signed and Sealed this

Twenty-eighth Day of September, 2010

David J. Kappos
*Director of the United States Patent and Trademark Office*